United States Patent
Rosen et al.

(10) Patent No.: US 7,211,562 B2
(45) Date of Patent: May 1, 2007

(54) METHODS FOR ENHANCING THE EFFICACY OF CYTOTOXIC AGENTS THROUGH THE USE OF HSP90 INHIBITORS

(75) Inventors: Neal Rosen, New York, NY (US); Pamela Nathalie Munster, Tampa, FL (US)

(73) Assignee: Sloan-Kettering Institute for Cancer Research, New York, NY (US)

( * ) Notice: Subject to any disclaimer, the term of this patent is extended or adjusted under 35 U.S.C. 154(b) by 191 days.

(21) Appl. No.: 10/415,878

(22) PCT Filed: Nov. 1, 2001

(86) PCT No.: PCT/US01/46304

§ 371 (c)(1), (2), (4) Date: May 1, 2003

(87) PCT Pub. No.: WO02/36171

PCT Pub. Date: May 10, 2002

(65) Prior Publication Data

US 2004/0110662 A1 Jun. 10, 2004

Related U.S. Application Data

(60) Provisional application No. 60/245,375, filed on Nov. 2, 2000.

(51) Int. Cl.
*A61K 35/00* (2006.01)
*A61K 41/00* (2006.01)
*A61K 38/00* (2006.01)

(52) U.S. Cl. ........................ 514/12; 424/114; 424/174.1
(58) Field of Classification Search .................... 514/2; 424/174.1, 114
See application file for complete search history.

(56) References Cited

U.S. PATENT DOCUMENTS 6,030,945 A * 2/2000 Ashkenazi .................. 514/12

OTHER PUBLICATIONS

Lai, L. et al. (2001) Feasibility of producing porcine nuclear transfer embryos by using G2/M-stage fetal fibroblasts as donors.□□Biol. Reprod. vol. 65, pp. 1558-1564.*
Jordan, A. et al. (1998) Tubulin as a target for anticancer drugs: agents which interact with the mitotic spindle.□□Med. Res. Rev. vol. 18, pp. 259-296. Review.*
Nguyen, D. M. et al. (1999) Sequence-dependent enhancement of paclitaxel toxicity in non-small cell lung cancer by 17-allylamino 17-demethoxygeldanamycin. J. Thorac. Cardiovasc. Surg. vol. 118, pp. 908-915.*
Munster, P. N. (2000) 17- allylamino-17-demethoxygeldanamycin (17-AAG) (17-AAG) inhibits intra-cellular Akt kinase activity in HER2 overexpressing breast cancer lines and enhances the apoptosis induced by cytotoxic agent, vol. 6, 4545s, Abstract No. 394.*
Otterson, G. A. et al. (1994) Absence of p16INK4 protein is restricted to the subset of lung cancer lines that retains wildtype RB. Oncogene. vol. 9, pp. 3375-3378.*
Schulte, T. W. et al. (1998) The benzoquinone ansamycin 17-allylamino-17-demethoxygeldanamycin binds to HSP90 and shares important biologic activities with geldanamycin. Cancer Chemother Pharmacol. vol. 42, pp. 273-279.*
Kroep J. R. et al. (Oct. 2000) Complete resection of the caudate lobe of the liver: technique and results. Br. J. Surg. vol. 83, pp. 1069-1076. Review.*
Srethapakdi, M. et al. (Jul. 2000) Inhibition of Hsp90 function by ansamycins causes retinoblastoma gene product-dependent G1 arrest. Cancer Res. vol. 60, pp. 3940-3946.*
Kylie, A. et al. (2002) Peloruside A, a novel antimitotic agent with paclitaxel-like microtubule- stabilizing activity. Cancer Res. vol. 62, pp. 3356-3360.*
Munster, P. N. et al. (2001) Modulation of Hsp90 function by ansamycins sensitizes breast cancer cells to chemotherapy-induced apoptosis in an RB- and schedule-dependent manner. Clin. Cancer Res., vol. 7, pp. 2228-2236.*
Brambilla et al. (2000) Semaphorin SEMA3F localization in malignant human lung and cell lines: A suggested role in cell adhesion and cell migration. Am. J. Pathol. vol. 156, No. 3, pp. 939-950.*

(Continued)

*Primary Examiner*—Kathleen M. Kerr
*Assistant Examiner*—Samuel Wei Liu
(74) *Attorney, Agent, or Firm*—Marina Larson & Associates, LLC

(57) ABSTRACT

The administration of cytotoxic agents followed by the administration of heat shock protein 90 inhibitors, such as ansamycins, has a synergistic effect on the growth inhibition of cells. This synergy occurs at doses of each cytotoxic agent that normally only causes minimal growth inhibition of cells. Such combination therapy thus allows one to use lower doses of cytotoxic agents to avoid or reduce their respective toxicity to patients without compromising their growth inhibitory effects. Thus, these combinations can be used for the treatment of an animal, preferably a mammal, that has a cell proliferative disorder, whether the cells have wild-type Rb or are Rb deficient or Rb negative. One such method, directed to treating cell proliferative disorders includes the step of administering a therapeutic effective amount of a cytotoxic agent followed by administering a therapeutic effective amount of a heat shock protein 90 inhibitor. The cytotoxic agent may be a microtubule-affecting agent, topoisomerase II inhibitor, a platinum complex, paclitaxel, or a paclitaxel derivative. The HSP90 inhibitor may be an ansamycin, radicicol or a synthetic compound that binds to the ATP-binding site of HSP90.

15 Claims, 4 Drawing Sheets

OTHER PUBLICATIONS

Hurst, S. et al., HSP90 Inhibitors block the mitotic checkpoint and are synergistically toxic with spindle poisons, Clinical Cancer Res. Nov. 1999, vol. 8, p. 3788s, #293.

Kherfellah, D. et al. Effect of the combination of topoisomerase I and topoisomerase II inhibitors on rat glioblastoma cells and drug-resistants. Pharmacol. Experimental Therapeutics. Mar. 1999. vol. 40, p. 109, #724.

Stebbins, C.E., et al. Crystal structure of the HSP-90 Geldanamycin complex: targeting of a protein chaperone by an antitumor agent. Cell. Apr. 1997. vol. 89, pp. 239-250, especially pp. 239-240 and 246-248.

Rosenhagen, M.C., et al. Synergistic inhibition of the Glucocorticoid receptor by padicicol and benzoquinone ansamycins. Biol. Chem. Mar. 2001. vol. 382, pp. 499-504, especially Figures 3 and 5.

Chavany, et al. "p185[erbB2] Binds to GRP94 in Vivo", Journal of Biological Chemistry, vol. 271, No. 9 Mar. 1, 1996, pp. 4974-4977.

Schnur, et al. "erbB-2 Oncogene Inhibition by Geldanamycin Derivatives: Synthesis, Mechanism of Action, and Structure—Activity Relationships", J. Med. Chem. 1995, 38, 3813-3820.

Neckers, "Effects of Geldanamycin and Other Naturally Occurring Small Molecule Antagonists of Heat Shock Protein 90 on HER2 Protein Expression", Breast Disease 11 (2000) 49-59. pp. 49-59.

Polkar, et al., Influence of cisplatin intrastrand crosslinking on the conformation, theremal stability, and energetics of a 20-mer DNA duplex. Proc. Natl. Acad. Sci. USA, vol. 93, pp. 7606-7611, Jul. '996.

\* cited by examiner

METHODS FOR ENHANCING THE EFFICACY OF CYTOTOXIC AGENTS THROUGH THE USE OF HSP90 INHIBITORS

This application is a 371 national phase of PCT application Ser. No. PCT/US01/46304 filed Nov. 1, 2001, published in English, and claims the benefit of U.S. Provisional Application Ser. No. 60/245,375 filed Nov. 2, 2000.

FIELD OF THE INVENTION

The present invention relates to the use of heat shock protein 90 (HSP90) inhibitors to enhance the efficacy of cytotoxic agents.

BACKGROUND OF THE INVENTION

Present treatments for cell proliferative diseases include surgery, treatment with cytotoxic agents, radiation, and combinations of the preceding. Treatment with cytotoxic agents, also referred to throughout this specification as antineoplastic agents or chemotherapeutic agents, often produces significant toxic side effects, including destruction of normal cells. Well-characterized toxicities include nausea and vomiting, myelosuppression, alopecia and mucosity. Serious cardiac problems are also associated with certain combinations of cytotoxic agents, e.g., doxorubicin and paclitaxel, but are less common.

Example classes of cytotoxic agents include, for example, the anthracycline family of drugs, the vinca alkaloids, the mitomycins, the bleomycins, the cytotoxic nucleosides, the taxanes, the epothilones, discodermolide, the pteridine family of drugs, diynenes and the podophyllotoxins. Members of those classes include, for example, doxorubicin, carminomycin, daunorubicin, aminopterin, methotrexate, methopterin, dichloromethotrexate, mitomycin C, porfiromycin, 5-fluorouracil, 6-mercaptopurine, gemcitabine, cytosine arabinoside, podophyllotoxin or podophyllotoxin derivatives, such as etoposide, etoposide phosphate or teniposide, melphalan, vinblastine, vincristine, leurosidine, vindesine, leurosine, paclitaxel and the like. Other useful antineoplastic agents include estramustine, cisplatin, carboplatin, cyclophosphamide, bleomycin, gemcitibine, ifosamide, melphalan, hexamethyl melamine, thiotepa, cytarabin, idatrexate, trimetrexate, dacarbazine, L-asparaginase, camptothecin, CPT-11, topotecan, ara-C, bicalutamide, flutamide, leuprolide, pyridobenzoindole derivatives, interferons and interleukins.

Taxanes and vinca alkaloid drugs are microtubule-affecting agents. Both taxanes and vinca alkaloids are based on naturally occurring compounds derived from plants. The taxanes are derived from the needles and twigs of the European yew, or the bark of the Pacific yew. Vinca alkaloids are derived from the periwinkle plant.

An example of a taxane is Taxol® (paclitaxel), which is a complex diterpene. Studies have shown that paclitaxel blocks and/or prolongs cells in the $G_2$ phase of the cell cycle. The inability of paclitaxel-treated cells to pass through $G_2$ of the cell cycle may result from paclitaxel binding to and stabilizing microtubules (Schiff, P. B. and Horwitz, S. B., 1980, *Proc. Natl Acad. Sci. USA*, 77:1561–1565). Stabilization of the microtubules prevents the normal reorganization of the microtubules necessary for interphase and mitotic functions (Wani et al., 1971, *J. Am. Chem. Soc.*, 93, 2325–2327; Schiff, P. B., supra). Taxol® also blocks the migration behavior of cells in culture (reference).

Paclitaxel has been shown to possess cytotoxicity and antitumor activity against certain cancers, including those not effectively treated by other cancer treatments. Further, paclitaxel was approved by the FDA in 1992 for the treatment of advanced ovarian cancer and in 1994 for the treatment of breast cancer. Paclitaxel is currently in clinical trials for the treatment other cancers, including lung cancer. Additionally, paclitaxel has been reported to increase the sensitivity of cells to the effects of ionizing radiation (see, U.S. Pat. No. 6,080,777).

Another class of antineoplastic agents are platinum complexes. Examples of such complexes are cisplatin and carboplatin. Platinum complexes are thought to disrupt DNA function by binding to DNA. For example, cisplatin kills tumor cells via formation of covalent, cross- or intrastrand DNA adducts (Sherman et al., 1987, *Chem. Rev.*, 87, 1153–81).

Platinum complexes are often associated with side effects. For example, Cisplatin treatment can result in renal toxicity. Additionally, Carboplatin treatment often results in hematologic toxicity. Both cisplatin and carboplatin can cause neurotoxic effects, and gastrointestinal distress, such as nausea and vomiting.

Yet another class of antineoplastic drugs are topoisomerase II inhibitors. At present the FDA has approved six antineoplastic drugs, which inhibit topoisomerase II. These drugs include doxorubicin, daunorubicin, idarubicin, mitoxantrone, etoposide, and anteniposide. Doxorubicin, idarubicin, and daunorubicin belong to the class of topoisomerase inhibitors known as anthracyclines. Mitoxantrone belongs to the class know as anthraquinone. Etoposide and teniposide belong to the class of compounds known as podophyllotoxin.

Anthracyclines antibiotics were initially isolated from fermentation products of *Streptomyce peucetus*. The most widely used anthracycline is doxorubicin. It is used in a wide variety of cancers, including lymphomas, breast cancer, sarcomas, Kaposi's sarcoma and leukemias. It is one of the primary drugs used for the treatment of breast cancer and soft tissue sarcomas.

Doxorubicin has serious side effects, including suppression of white blood cell and platelet formation. Doxorubicin can also cause heart damage due to the formation of free-radical intermediates which destroy myocardial cells. All patients who take doxorubicin suffer hair loss.

Another class of antineoplastic agents are the ansamycins. Ansamycin antibiotics are natural products derived from *Streptomyces hygroscopicus* that have profound effects on eukaryotic cells. The ansamycins were originally isolated on the basis of their ability to revert v-src transformed fibroblasts (Uehara, Y. et al., 1985, *J. Cancer Res.*, 76: 672–675). Subsequently, they were shown to have antiproliferative effects on cells transformed with a number of oncogenes, particularly those encoding tyrosine kinases (Uehara, Y., et al., 1988, *Virology*, 164: 294–98). inhibition of cell growth is associated with apoptosis and, in certain cellular systems, with induction of differentiation (Vasilevskaya, A. et al., 1999, *Cancer Res.*, 59: 3935–40). An ansamycin derivative, 17-allylamino 17-demethoxygeldanamycin (17-AAG), is currently in phase I clinical trials. The use of ansamycins as anticancer agents are described in U.S. Pat. Nos. 4,261,989, 5,387,584 and 5,932,566. The preparation of the ansamycin, geldanamycin, is described in U.S. Pat. No. 3,595,955 (incorporated herein by reference).

The eukaryotic heat shock protein 90s (HSP90s) are ubiquitous chaperone proteins, which bind and hydrolyze ATP. The role of HSP90s in cellular functions are not completely understood, but recent studies indicate that HSP90s are involved in folding, activation and assembly of a wide range of proteins, including key proteins involved in signal transduction, cell cycle control and transcriptional regulation. For example, researchers have reported that HSP90 chaperone proteins are associated with important signaling proteins, such as steroid hormone receptors and protein kinases, including many implicated in tumorigenesis, such as Raf-1, EGFR, v-Src family kinases, Cdk4, and ErbB-2 (Buchner J., 1999, *TIBS*, 24:136–141; Stepanova, L. et al., 1996, *Genes Dev.* 10:1491–502; Dai, K. et al., 1996, *J. Biol. Chem.* 271:22030–4).

In vivo and in vitro studies indicate that without the aid of co-chaperones HSP90 is unable to fold or activate proteins. For steroid receptor conformation and association in vitro, HSP90 requires Hsp70 and p60/Hop/Sti1 (Caplan, A., 1999, *Trends in Cell Biol.*, 9: 262–68). In vivo HSP90 may interact with HSP70 and its co-chaperones. Other co-chaperones associated with HSP90s in higher eukaryotes include Hip, Bag1, HSP40/Hdj2/Hsj1, Immunophillins, p23, and p50 (Caplan, A. supra).

Many ansamycins, such as herbimycin A (HA) and geldanamycin (GM), bind tightly to a pocket in the HSP90s (Stebbins, C. et al., 1997, *Cell*, 89:239–250). The binding of ansamycins to HSP90 has been reported to inhibit protein refolding and to cause the proteasome dependent degradation of a select group of cellular proteins (Sepp-Lorenzino, L., et al., 1995, *J. Biol. Chem.*, 270:16580–16587; Whitesell, L. et al., 1994, *Proc. Natl. Acad. Sci. USA*, 91: 8324–8328).

The ansamycin-binding pocket in the N-terminus of Hsp90 is highly conserved and has weak homology to the ATP-binding site of DNA gyrase (Stebbins, C. et al., supra; Grenert, J. P. et al., 1997, *J. Biol. Chem.*, 272:23843–50). This pocket has been reported to bind ATF and ADP with low affinity and to have weak ATPase activity (Proromou, C. et al., 1997, *Cell*, 90: 65–75; Panaretou, B. et al., 1998, *EMBO J.*, 17: 4829–36). In vitro and in vivo studies indicate that occupancy of the pocket by ansamycins alters HSP90 function and inhibits protein refolding. At high concentrations, ansamycins have been reported to prevent binding of protein substrates to HSP90 (Scheibel, T., H. et al, 1999, *Proc. Natl. Acad. Sci. USA* 96:1297–302; Schulte, T. W. et al., 1995, *J. Biol. Chem.* 270:24585–8; Whitesell, L., et al., 1994, *Proc. Natl. Acad. Sci USA* 91:8324–8328). Alternatively, they have also been reported to inhibit the ATP-dependent release of chaperone-associated protein substrates (Schneider, C., L. et al., 1996, *Proc. Natl. Acad. Sci. USA*, 93:14536–41; Sepp-Lorenzino et al., 1995, *J. Biol. Chem.* 270:16580–16587). In both models, the unfolded substrates are degraded by a ubiquitin-dependent process in the proteasome (Schneider, C., L., supra; Sepp-Lorenzino, supra.) Therefore, ansamycins act as generalized inhibitors of HSP90 function or as agents that mimic or antagonize the regulatory effects of endogenous ligands that bind to the pocket.

In both tumor and nontransformed cells, binding of ansamycins to HSP90 has been reported to result in the degradation of a subset of signaling regulators. These include Raf (Schulte, T. W. et al., 1997, *Biochem. Biophys. Res. Commun.* 239:655–9; Schulte, T. W., et al., 1995, *J. Biol Chem.* 270:24585–8), nuclear steroid receptors (Segnitz, B., and U. Gehring. 1997, *J Biol. Chem.* 272:18694–18701; Smith, D. F. et al., 1995, *Mol. Cell. Biol.* 15:6804–12), v-src (Whitesell, L., et al., 1994, *Proc. Natl. Acad. Sci. USA* 91:8324–8328) and certain transmembrane tyrosine kinases (Sepp-Lorenzino, L. et al., 1995, *J. Biol. Chem.* 270: 16580–16587) such as EGF receptor (EGFR) and Her2/Neu (Hartmann, F., et al., 1997, *Int. J. Cancer* 70:221–9; Miller, P. et al., 1994, *Cancer Res.* 54:2724–2730; Mimnaugh, E. G., et al., 1996, *J. Biol. Chem.* 271:22796–801; Schnur, R. et al., 1995, *J. Med. Chem.* 38:3806–3812). The ansamycin-induced loss of these proteins is said to lead to the selective disruption of certain regulatory pathways and results in growth arrest at specific phases of the cell cycle (Muise-Heimericks, R. C. et al., 1998, *J. Biol Chem.* 273:29864–72).

Combination therapy utilizing 17-AAG for the treatment of certain cancers has been discussed. For example, Nguyen, D. et al., 1999, *Journal Thoracic and Cardiovascular Surgery*, 118:908–915, report that concurrent treatment of non-small cell lung cancer cells in vitro with 17-AAG and Taxol® enhances the toxicity of paclitaxel.

Cyclin D in complex with Cdk4 or Cdk6 and cyclin E-Cdk2 phosphorylate the protein product of the retinoblatoma gene, Rb. Researchers have reported that the protein product of the Rb gene is a nuclear phosphoprotein, which arrests cells during the $G_1$ phase of the cell cycle by repressing transcription of genes involved in the $G_1$ to S phase transition (Weinberg, R. A., 1995, *Cell*, 81:323–330). Dephosphorylated Rb inhibits progression through late $G_1$, in part, through its interaction with E2F transcription family members, which ultimately represses the transcription of E2F target genes Dyson, N., 1998, *Genes Dev.*, 12: 2245–2262). Progressive phosphorylation of Rb by the cyclin-dependent kinases in mid to late $G_1$ leads to dissociation of Rb from Rb-E2F complexes, allowing the expression of E2F target genes and entry into the S phase.

The retinoblastoma gene product is mutated in several tumor types, such as retinoblastoma, osteosarcoma and small-cell lung cancer. Research also indicates that in many additional human cancers the function of Rb is disrupted through neutralization by a binding protein, (e.g., the human papilloma virus-E7 protein in cervical carcinoma; Ishiji, T, 2000, *J Dermatol.*, 27: 73–86) or deregulation of pathways ultimately responsible for its phosphorylation. Inactivation of the Rb pathway often results from perturbation of p16INK4a, Cyclin D1, and Cdk4.

Most cancer therapies are not successful with all types of cancers. For example, solid tumor types ultimately fail to respond to either radiation or chemotherapy, so there remains a need for cancer treatments which target specific cancer types. Further, the treatment of cancers and other cell proliferative diseases usually requires the use of cytotoxic agents, which have severe side effects. Therefore, a need exists for more effective treatments, especially those with fewer adverse side effects than currently available. The present invention satisfies these needs and provides related advantages as well. The present invention provides novel methods for treating cell proliferative disorders through the use of ansamycins in combination with cytotoxic agents.

SUMMARY OF THE INVENTION

It has been discovered that, surprisingly, the administration of cytotoxic agents followed by the administration of heat shock protein 90 inhibitors, such as ansamycins, has a synergistic effect on the growth inhibition of cells. This synergy occurs at doses of each cytotoxic agent that normally only causes minimal growth inhibition of cells. Such combination therapy thus allows one to use lower doses of cytotoxic agents to avoid or reduce their respective toxicity to patients without compromising their growth inhibitory effects.

One aspect of the invention relates to methods useful for the treatment of an animal, preferably a mammal, that has a cell proliferative disorder. One such method, directed to treating cell proliferative disorders associated with wild-type Rb cells, comprises administration of a therapeutic effective amount of a cytotoxic agent followed by administering a therapeutic effective amount of a heat shock protein 90 inhibitor. Preferably, the cytotoxic agent is a microtubule-affecting agent, topoisomerase II inhibitor, or a platinum complex. More preferably, the cytotoxic agent is paclitaxel, or a paclitaxel derivative. In a preferred embodiment, the HSP90 inhibitor is an ansamycin, radicicol or a synthetic compound that binds to the ATP-binding site of HSP90. In a particularly preferred embodiment, the ansamycin is 17-AAG (CNF-101) or a derivative thereof. When the cytotoxic agent is doxorubicin, the administration is not schedule dependent, i.e., doxorubicin can be administered before, concurrently, or after the HSP90 inhibitor.

The invention also relates to methods useful for the treatment of an animal, preferably a mammal, that has a cell proliferative disorder associated with cells that are Rb deficient or Rb negative. One such method comprises, administering a therapeutically effective amount of a HSP90 inhibitor before or after the administration of a cytotoxic agent. Preferably, the cytotoxic agent is a microtubule-affecting agent, a platinum complex, or a topoisomerase II inhibitor. More preferably, the cytotoxic agent is paclitaxel, a paclitaxel derivative, or doxorubicin or doxorubicin derivative. In a preferred embodiment, the HSP90 inhibitor is an ansamycin, radicicol or a synthetic compound that binds to the ATP-binding site of HSP90. In a particularly preferred embodiment, the ansamycin is CNF-101 or a derivative thereof.

The present invention further provides methods of destroying cells with wild-type Rb. In one such embodiment, the method comprises administering to appropriate cells an effective amount of a cytotoxic agent followed by the administration of an effective amount of a HSP90 inhibitor. In one embodiment, the HSP90 inhibitor is an ansamycin, radicicol, or a synthetic compound that binds to the ATP-binding site of HSP90. In a particularly preferred embodiment, the ansamycin is CNF-101 or a derivative thereof. In especially preferred embodiments, the ansamycin is given in conjunction with paclitaxel, a paclitaxel derivative, doxorubicin, or a doxorubicin derivative. When the cytotoxic agent is doxorubicin, the administration is not schedule dependent, i;e., doxorubicin can be administered before, concurrently, or after the HSP90 inhibitor.

In another embodiment, the invention is a method of destroying cells, which are retinoblastoma negative or deficient cells, comprising administering a therapeutically effective amount of a HSP90 inhibitor and a cytotoxic agent. Preferably, the cytotoxic agent is a microtubule-affecting agent, platinum complex or topoisomerase II inhibitor. More preferably, the cytotoxic agent is paclitaxel, a paclitaxel derivative, or doxorubicin. In a particularly preferred embodiment, the HSP90 inhibitor is an ansamycin, radicicol or a synthetic compound that binds to the ATP-binding site of HSP90. In an especially preferred embodiment, the ansamycin is CNF-101 or a derivative thereof.

In a preferred embodiment, the present invention provides a method of treating a cell proliferative diseases, such as breast cancer, or small-cell lung cancer.

The methods can further comprise treating a mammal in combination with other therapies. Other such therapies include, but are not limited to, surgery, treatment with other cytotoxic agents and radiotherapy.

By means of the invention, a method of enhancing the efficacy of cytotoxic agents is provided. The present invention also provides novel methods for treating cell proliferative disorders and other conditions associated with retinoblastoma negative or deficient cells. These and other advantages of the present invention will be appreciated from the detailed description and examples set forth below. The detailed description and examples enhance the understanding of the invention, but are not intended to limit the scope of the invention.

BRIEF DESCRIPTION OF THE FIGURES

FIG. 3A shows increasing concentrations of Taxol® with or without 50 nM of 17-AAG.

DETAILED DESCRIPTION OF THE INVENTION

Figure 1C:
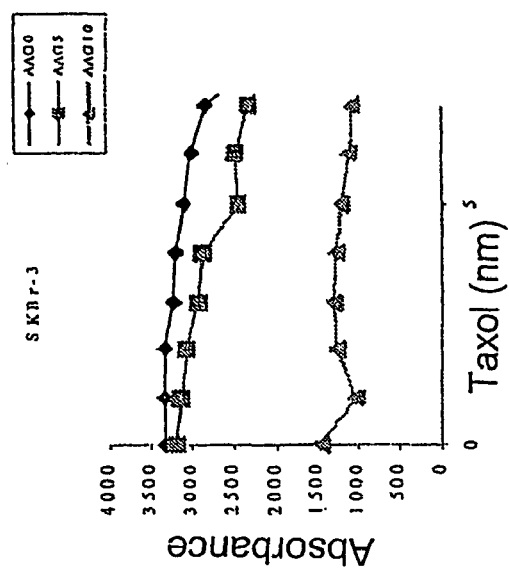
FIGS. 1A–C show the effect of three concentrations of CNF-101 (17-AAG) in combination with increasing concentrations of (A) Cisplatin, (B) Doxorubicin, or (C) Taxol® on growth of SKBR3 breast cancer cells.

The present invention concerns the surprising discovery that certain combinations of heat shock protein 90 (HSP90) inhibitors and cytotoxic agents have a synergistic effect on the growth inhibition of cells. This synergy occurs at doses of each cytotoxic agent that normally only causes minimal growth inhibition of cells. This discovery will aid in the treatment of cell proliferative disorders.

As used herein "HSP90" refers to the HSP90 family of proteins, including, but not limited to, HSP90 alpha and beta, Grp94, and Trap-1.

For purposes of this invention, two drugs are considered therapeutically synergistic if a combination regimen produces a therapeutic effect that is better than the therapeutic effect of each agent administered alone at optimal or maximum tolerated doses.

The term "cytotoxic agent" refers to any compound mediating cell death by any mechanism including, but not limited to, apoptosis, inhibition of metabolism or DNA synthesis, interference with cytoskeletal organization, destabilization or chemical modification of DNA, etc.

"Cell proliferative disorders" refer to disorders wherein unwanted cell proliferation of one or more subset(s) of cells in a multicellular organism occurs, resulting in harm, for example, pain or decreased life expectancy to the organism. Cell proliferative disorders include, but are not limited to, tumors, benign tumors, blood vessel proliferative disorders, autoimmune disorders and fibrotic disorders.

When the methods of the present invention are used in conjunction with cell proliferative disorders associated with Rb deficient or Rb negative cells, the enhancement by the HSP90 inhibitor is schedule independent, i.e., the HSP90 inhibitor can be given either before, concurrently or after the cytotoxic agent. When the methods of the present invention are used to treat a cell proliferative disorders associated with wild-type Rb cells, the enhancement by the HSP90 inhibitor is schedule dependent, i.e., the HSP90 inhibitor is given after the cytotoxic agent, preferably 1 to 4 hours after, more preferably 6 to 12 hours after and even more preferably 12 to 18 hours after. In the case of cytotoxic agents which are not $G_2/M$-acting drugs, the enhancement by the HSP90 inhibitor is schedule independent regardless of whether the cells have wild-type Rb or are Rb deficient or Rb negative.

Examples of cytotoxic agents which are $G_2/M$ acting drugs include, but are not limited to, bleomycin (in some cells), vinca alkaloids (e.g., vincristine, vinblastine), taxanes (e.g., paclitaxel, docetaxel).

Examples of cytotoxic agents which act in the S phase include, but are not limited to, antimetabolites, DNA intercalators, alkylating agents, topoisomerase inhibitors (e.g., cytarabine, doxorubicin, methotrexate, 6-marcaptopurine, 6-thioguanine, hydroxyurea, prednisone, procarbazine). $G_1$-phase cytotoxic agents include, but are not limited to, aspariginase, diglycoaldehyde, and corticisteroids.

The term "Rb deficient or Rb negative" describes several types of cell. First, a cell which does not contain a functional Rb gene. Second, a cell that can encode a Rb protein, but in which the protein does not function properly or is produced at lower than normal level. Third, a Rb deficient phenotype can also occur due to the perturbation of the pathway, which ultimately results in phosphorylation of the Rb protein, for example, perturbation of p16INK4a, Cyclin D1, or Cdk4.

The term "effective amount" as used herein, means an amount of compounds utilized in the methods of the present invention which are capable of providing a therapeutic effect. The specific dose of the compounds administered according to this invention to obtain therapeutic and/or prophylactic effects will, of course, be determined by the particular circumstances surrounding the case, including, for example, the compounds administered, the route of administration, the condition being treated and the individual being treated. A typical daily dose (administered in single or divided doses) will contain a dosage level of from about 0.01 mg/kg to about 50 mg/kg of body weight of an active compound of this invention. Preferred daily doses generally will be from about 0.05 mg/kg to about 20 mg/kg and ideally from about 0.1 mg/kg to about 10 mg/kg.

The preferred therapeutic effect of the methods of the instant invention, with respect to cell proliferative disorders, is the inhibition, to some extent; of growth of cells causing or contributing to a cell proliferative disorder. A therapeutic effect relieves to some extent one or more of the symptoms of a cell proliferative disorder. In reference to the treatment of a cancer, a therapeutic effect refers to one or more of the following: 1) reduction in the number of cancer cells; 2) reduction in tumor size; 3) inhibition (i.e., slowing to some extent, preferably stopping) of cancer cell infiltration into peripheral organs; 3) inhibition (i.e., slowing to some extent, preferably stopping) of tumor metastasis; 4) inhibition, to some extent, of tumor growth; and/or 5) relieving to some extent one or more of the symptoms associated with the disorder.

In reference to the treatment of a cell proliferative disorder other than a cancer, a therapeutic effect refers to either: 1) the inhibition, to some extent, of the growth of cells causing the disorder; 2) the inhibition, to some extent, of the production of factors (e.g., growth factors) causing the disorder; and/or 3) relieving to some extent one or more of the symptoms associated with the disorder.

The methods of this invention are useful for inhibiting cell proliferative diseases associated with Rb negative or Rb deficient cells, for example, retinoblastoma, osteosarcoma, breast cancers, bladder cancer, prostate cancer, renal carcinoma, cancers associated with viral infections, such as cervical cancers associated with human papilloma virus, and small-cell lung cancer.

The methods of the present invention may be used on animals, preferably said animals are mammals, and more preferably said mammals are humans.

The methods of the inventions may be used either alone or in combination with other therapies or methods useful for treating a particular cell proliferative disorder.

The use of the present invention is facilitated by identifying whether the cell proliferative disorder is accompanied by cells, which contain altered expression of the Rb gene product. Once such disorders are identified, patients suffering from such a disorder can be identified by analysis of their symptoms by procedures well known to medical doctors. Such patients can then be treated as described herein.

The determination of whether the cell proliferation disorder is associated with an altered expression of the Rb gene product can be carried out by first determining the protein expression of Rb in the appropriate cells isolated from a mammal suspected of having a cell proliferative disorder or viral infection. For example, in the case of small-cell lung cancer, the protein expression of Rb determined from cells isolated from a mammal suspected of having small-cell lung cancer can be compared to the appropriate cells isolated from a disease free mammal. Rb expression and/or mutations can be measured using methods well known in the art, including, but not limited to, immunohistochemistry, Southern blot analysis, and Northern blot analysis. The use of immunohistochemistry (eg., Western blot analysis) to determine Rb expression is described by Higashiyam M et al., 1994, *Oncogene,* 51: 544–51, and Kohn G. J et al., 1997, *J. Gastroenterol Hepatol.,* 12: 198–203, both of these references are incorporated herein by reference in their entireties. The use of Southern blot analysis to determine defects in the Rb gene is demonstrated by Presti J. C. Jr. et al., 1996, *Anticancer Res.,* 16:549–56, which is incorporated herein by reference in its entirety. The determination of Rb mRNA using Northern blot analysis is demonstrated by Rygaard K. et al., 1990, *Cancer Res.,* 50: 5312–7, which is incorporated by reference herein in its entirety. If the analysis indicates that there is altered Rb expression, the patient is a candidate for treatment using the methods described herein.

In the case of cell proliferative disorders arising due to unwanted proliferation of non-cancer cells, the level of the Rb gene product is compared to that level occurring in the general population (e.g., the average level occurring in the general population of people or animals excluding those people or animals suffering from a cell proliferative disorder). If the unwanted cell proliferation disorder is characterized by an abnormal level of Rb than occurring in the general population, then the disorder is a candidate for treatment using the methods described herein.

Cell proliferative disorders include those listed above. These disorders are not necessarily independent. For example, fibrotic disorders may be related to, or overlap with, blood vessel disorders. For example, atherosclerosis (which is characterized herein as a blood vessel disorder) is associated with the abnormal formation of fibrous tissue.

A cancer cell refers to various types of malignant neoplasms, most of which can invade surrounding tissues, and may metastasize to different sites, as defined by Stedman's Medical Dictionary 25th edition (Hensyl ed. 1990).

The formation and spreading of blood vessels, or vasculogenesis and angiogenesis respectively, play important roles in a variety of physiological processes such as embryonic development, wound healing and organ regeneration. They also play a role in cancer development. Blood vessel proliferation disorders refer to angiogenic and vasculogenic disorders generally resulting in abnormal proliferation of blood vessels. Examples of such disorders include restenosis, retinopathies, and atherosclerosis.

As noted above, other such proliferative diseases can be identified by standard techniques, and by determination of the efficacy of action of the compounds described herein.

A. Synergistic Effects of CNF-101 in Combination with Conventional Chemotherapeutic Agents in Breast Cancer Cells: Effect of Drug Dose, Schedule and Rb Status On Antiproliferative Activity, Apoptosis and Cell-Cycle Blockade in SKBR-3.

Figure 1B:
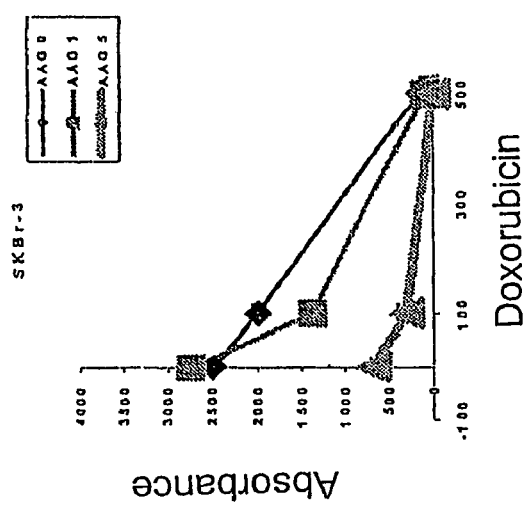
Figure 1A:
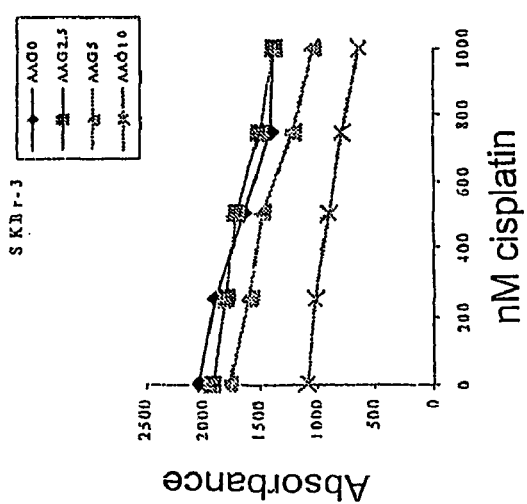

As described herein and the examples that follow, the addition of CNF-101 to cultured breast cancer cells enhanced the growth inhibition caused by several chemotherapeutic agents, including the DNA intercalating antibiotic doxorubicin (a topoisomerase II inhibitor), the microtubule-affecting paclitaxel and the DNA cross-linking agent cisplatin. These studies were performed at doses that cause minimal growth inhibition of each drug alone in order to demonstrate potential additive or synergistic effects, since higher doses of either drug produced complete growth inhibition induced by CNF-101 or the cytotoxic drug. The addition of 1–10 nM to cisplatin in SKBr-3 breast cancer cells caused growth inhibition that was additive. In contrast, treatment of SKBr-3 breast cancer cells with CNF-101 and Taxol® or doxorubicin caused synergistic growth inhibitory effects (FIGS. 1A–C).

The synergistic effects of Taxol® and CNF-101 are due to enhanced induction of apoptosis. Exposure of cells to CNF-101 alone resulted in a relatively small increase in the number of apoptotic nuclei as compared to cells treated with CNF-101 and either Taxol® or doxorubicin.

Figure 4:
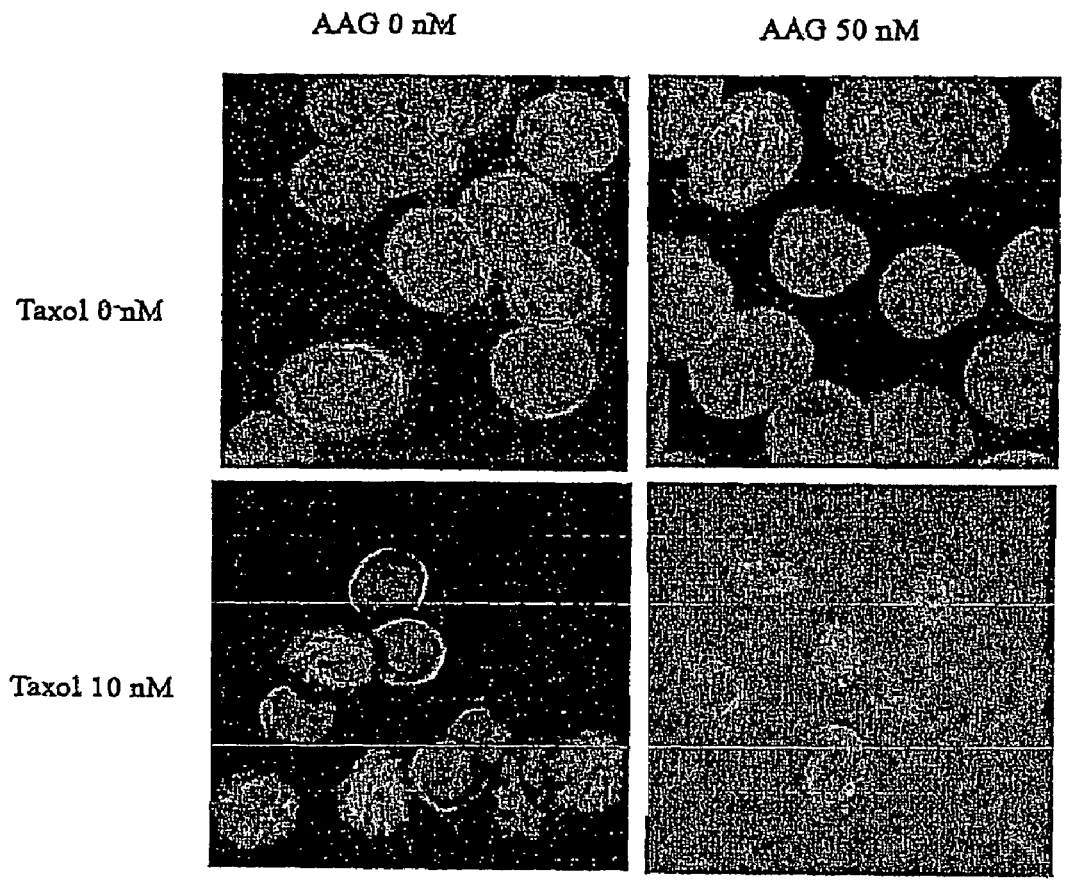
FIG. 4 shows differential effects of Taxol®, CNF-101 (17-AAG) and the combination of both agents on spindle formation and apoptosis in SKBR-3 cells.

The effects of Taxol®, CNF-101 and a combination of the two agents on nuclear fragmentation (a marker of apoptosis) and mitotic spindle formation in SKBR-3 cells demonstrated that Taxol® acts by disrupting mitotic spindle formation. CNF-101, however, has no effect on the spindle formation but instead enhances the cellular apoptotic response to spindle disruption (FIG. 4).

The synergistic effects of CNF-101 and Taxol® were found to be schedule dependent in cells with wild-type Rb. Synergy occurred when cells were treated first with Taxol® followed by treatment with CNF-101. Without wishing to be bound to a particular theory, the schedule dependence of synergy between CNF-101 and cytotoxic agents only applied to cytotoxic agents that act in the $G_2$/M of the cell cycle, such as Taxol®. For example, when CNF-101 was combined with a DNA damaging agent, such as doxorubicin, synergy was seen irrespective of the order of drug administration. Similarly in Rb negative or deficient cells, synergy between CNF-101 and cytotoxic agent was schedule independent.

B. Administration and Pharmaceutical Compositions

The compounds utilized in the methods of the instant invention may be administered either alone or, preferably, in combination with pharmaceutically acceptable carriers, excipients or diluents, in a pharmaceutical composition, according to standard pharmaceutical practice. The compounds can be administered orally or parenterally, including the intravenous, intramuscular, intraperitoneal, subcutaneous, rectal and topical routes of administration.

The pharmaceutical compositions used in the methods of the instant invention can contain the active ingredient in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients, which are suitable for the manufacture of tablets. These excipients may be for example, inert diluents, such as calcium carbonate, sodium carbonate, lactose, calcium phosphate or sodium phosphate; granulating and disintegrating agents, for example, microcrystalline cellulose, sodium crosscarmellose, corn starch, or alginic acid; binding agents, for example starch, gelatin, polyvinyl-pyrrolidone or acacia, and lubricating agents, for example, magnesium stearate, stearic acid or talc. The tablets may be uncoated or they may be coated by known techniques to mask the unpleasant taste of the drug or delay disintegration and absorption in the gastrointestinal tract and thereby provide a sustained action over a longer period. For example, a water soluble taste masking material such as hydroxypropylmethyl-cellulose or hydroxypropylcellulose, or a time delay material such as ethyl cellulose, cellulose acetate butyrate may be employed.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water soluble carrier such as polyethyleneglycol or an oil medium, for example peanut oil, liquid paraffin, or olive oil.

Aqueous suspensions contain the active material in admixture with excipients suitable for the manufacture of aqueous suspensions. Such excipients are suspending agents, for example sodium carboxymethylcellulose, methylcellulose, hydroxypropylmethyl-cellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethylene-oxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl p-hydroxybenzoate, one or more coloring agents, one or more flavoring agents, and one or more sweetening agents, such as sucrose, saccharin or aspartame.

Oily suspensions may be formulated by suspending the active ingredient in a vegetable oil, for example, arachis oil, olive oil, sesame oil or coconut oil, or in mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as butylated hydroxyanisol or alpha-tocopherol.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present. These compositions may be preserved by the addition of an anti-oxidant such as ascorbic acid.

The pharmaceutical compositions used in the methods of the instant invention may also be in the form of oil-in-water emulsions. The oily phase may be a vegetable oil, for example olive oil or arachis oil, or a mineral oil, for example liquid paraffin or mixtures of these. Suitable emulsifying agents may be naturally occurring phosphatides, for example soy bean lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening, flavoring agents, preservatives and antioxidants.

Syrups and elixirs may be formulated with sweetening agents, for example glycerol, propylene glycol, sorbitol or sucrose. Such formulations may also contain a demulcent, a preservative, flavoring and coloring agents and antioxidant.

The pharmaceutical compositions may be in the form of sterile injectable aqueous solutions. Among the acceptable vehicles and solvents that may be employed are water, Ringer's solution and isotonic sodium chloride solution.

The sterile injectable preparation may also be a sterile injectable oil-in-water microemulsion where the active ingredient is dissolved in the oily phase. For example, the active ingredient may be first dissolved in a mixture of soybean oil and lecithin. The oil solution then introduced into a water and glycerol mixture and processed to form a microemulsion.

The injectable solutions or microemulsions may be introduced into a patient's blood stream by local bolus injection. Alternatively, it may be advantageous to administer the solution or microemulsion in such a way as to maintain a constant circulating concentration of the instant compound. In order to maintain such a constant concentration, a continuous intravenous delivery device may be utilized. An example of such a device is the Deltec CADD-PLUS™ model 5400 intravenous pump.

The pharmaceutical compositions may be in the form of a sterile injectable aqueous or oleagenous suspension for intramuscular and subcutaneous administration. This suspension may be formulated according to the known art using those suitable dispersing or wetting agents and suspending agents which have been mentioned above. The sterile injectable preparation may also be a sterile injectable solution or suspension in a non-toxic parenterally acceptable diluent or solvent, for example as a solution in 1,3-butane diol. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The HSP90 inhibitors and cytotoxic agents used in the methods of the present invention may also be administered in the form of suppositories for rectal administration of the drug. These compositions can be prepared by mixing the inhibitors with a suitable non-irritating excipient which is solid at ordinary temperatures but liquid at the rectal temperature and will therefore melt in the rectum to release the drug. Such materials include cocoa butter, glycerinated gelatin, hydrogenated vegetable oils, mixtures of polyethylene glycols of various molecular weights and fatty acid esters of polyethylene glycol.

For topical use, creams, ointments, jellies, solutions or suspensions, etc., containing an HSP90 inhibitor or cytotoxic agent can be used. (As used herein, topical application can include mouthwashes and gargles.)

The compounds used in the methods of the present invention can be administered in intranasal form via topical use of suitable intranasal vehicles and delivery devices, or via transdermal routes, using those forms of transdermal skin patches well known to those of ordinary skill in the art. To be administered in the form of a transdermal delivery system, the dosage administration will, of course, be continuous rather than intermittent throughout the dosage regimen.

The methods of the present invention may also be useful with other agents that inhibit angiogenesis and thereby inhibit the growth and invasiveness of tumor cells, including, but not limited to, VEGF receptor inhibitors, angiostatin and endostatin.

When compounds used in the methods of the present invention are administered into a human subject, the daily dosage will normally be determined by the prescribing physician with the dosage generally varying according to the age, weight, and response of the individual patient, as well as the severity of the patient's symptoms.

In one exemplary application, a suitable amount of a HSP90 inhibitor and cytotoxic agent is administered to a mammal undergoing treatment for cancer. Administration occurs in an amount of each type of inhibitor of between about 0.1 mg/kg of body weight to about 60 mg/kg of body weight per day, preferably of between 0.5 mg/kg of body weight to about 40 mg/kg of body weight per day. A particular therapeutic dosage that comprises the instant composition includes from about 0.01 mg to about 1000 mg of a HSP90 inhibitor or cytotoxic agent. Preferably, the dosage comprises from about 1 mg to about 1000 mg of a HSP90 inhibitor or cytotoxic agent.

Examples of cytotoxic agents, which can be used in conjunction with the methods of the present invention include, in general, microtubule-affecting agents (such as paclitaxel (also known as Taxol®), docetaxel (also known as Taxotere®), or their derivatives); alkylating agents, antimetabolites; epidophyllotoxin; an antineoplastic enzyme; a topoisomerase inhibitor; procarbazine; mitoxantrone; platinum complexes; biological response modifiers and growth inhibitors; hormonal/anti-hormonal therapeutic agents and haematopoietic growth factors.

Example classes of cytotoxic agents include, for example, the anthracycline family of drugs, the vinca drugs, the mitomycins, the bleomycins, the cytotoxic nucleosides, the taxanes, the epothilones, discodermolide, the pteridine family of drugs, diynenes and the podophyllotoxins. Particularly useful members of those classes include, for example, doxorubicin, carminomycin, daunorubicin, aminopterin, methotrexate, methopterin, dichloromethotrexate, mitomycin C, porfiromycin, 5-fluorouracil, 6-mercaptopurine, gemcitabine, cytosine arabinoside, podophyllotoxin or podophyllotoxin derivatives such as etoposide, etoposide phosphate or teniposide, melphalan, vinblastine, vincristine, leurosidine, vindesine, leurosine, paclitaxel and the like. Other useful antineoplastic agents include estramustine, cisplatin, carboplatin, cyclophosphamide, bleomycin, gemcitibine, ifosamide, melphalan, hexamethyl melamine, thiotepa, cytarabin, idatrexate, trimetrexate, dacarbazine, L-asparaginase, camptothecin, CPT-11, topotecan, ara-C, bicalutamide, flutamide, leuprolide, pyridobenzoindole derivatives, interferons and interleukins.

Microtubule-affecting agents useful in the invention are well known to those of skill in the art and include, but are not limited to, allocolchicine, halichondrin B, colchicine, colchicine derivatives, dolastatin 10, maytansine, rhizoxin, paclitaxel (Taxol®, Taxol® derivatives, thiocolchicine, trityl cysteine, vinblastine sulfate, vincristine sulfate, epothione A, epothilone, and discodermolide, estramusinte, nocodazole, and the like. Examples of such compounds are described in U.S. Pat. No. 6,100,411; and U.S. Pat. No. 6,096,757 and are also described in the scientific literature, see, e.g., Bulinski (1997) *J. Cell Sci.* 110:3055–3064; Panda (1997) *Proc. Natl. Acad. Sci. USA* 94:10560–10564; Muhlradt (1997) *Cancer Res.* 57:3344–3346; Nicolaou (1997) *Nature* 387:268–272; Vasquez (1997) *Mol. Biol. Cell* 8:973–985; Panda (1996) *J. Biol. Chem.* 271:29807–29812.

Particularly preferred microtubule-affecting agents are those with paclitaxel-like activity. These include, but are not limited to paclitaxel and paclitaxel derivatives (paclitaxel-like compounds) and analogs. Paclitaxel and its derivatives are available commercially. In addition, methods of making paclitaxel and paclitaxel derivatives and analogs are well known to those of skill in the art (see, e.g., U.S. Pat. Nos. 5,569,729; 5,565,4778; 5,530,020; 5,527,924; 5,508,447; 5,489,589; 5,488,116; 5,484,809; 5,478,854; 5,478,736; 5,475,120; 5,468,769; 5,461,169; 5,440,057; 5,422,364; 5,411,984; 5,405,972; and 5,296,506.

Pharmaceutical compositions of Taxol® and Taxol® derivatives are known to those skilled in the art, for example, pharmaceutical compositions of Taxol® or Taxol® derivatives are described in the following U.S. Pat. Nos. 6,090,955; 6,090,844; 5,648,090; and 5,415,869.

Examples of HSP90 inhibitors which can be used with the methods of the present invention include, but are not limited to, quinone ansamycin antibiotics, such as the macbecins, geldanamycin, including derivatives of geldanamycin, such as 17-AAG, herbimycin A, radicicol, and synthetic compounds that can bind into the ATP-binding site of HSP90.

Methods for the safe and effective administration of most of these cytotoxic agents are known to those skilled in the art. In addition, their administration is described in the standard literature. For example, the administration of many of the cytotoxic agents listed herein is described in the "Physicians' Desk Reference, e.g., 2000 edition (Medical Economics Company, Montvale, N.J. 07645–1742, USA); which is incorporated herein by reference.

Preferably, the pharmaceutical preparation is in unit dosage form. In such form, the preparation is subdivided into unit doses containing appropriate quantities of the active component, e.g., an effective amount to achieve the desired purpose.

The quantity of active compound in a unit dose of preparation may be varied or adjusted from about 0.1 mg to 1000 mg, preferably from about 1 mg to 300 mg, more preferably 10 mg to 200 mg, according to the particular application.

The actual dosage employed may be varied depending upon the requirements of the patient and the severity of the condition being treated. Determination of the proper dosage for a particular situation is within the skill of the art. Generally, treatment is initiated with smaller dosages which are less than the optimum dose of the compound. Thereafter, the dosage is increased by small amounts until the optimum effect under the circumstances is reached. For convenience, the total daily dosage may be divided and administered in portions during the day if desired.

The amount and frequency of administration of the compounds used in the methods of the present invention and-if applicable other chemotherapeutic agents and/or radiation therapy will be regulated according to the judgment of the attending clinician (physician) considering such factors as age, condition and size of the patient as well as severity of the disease being treated. A dosage regimen of the HSP90 inhibitor or cytotoxic agent can be oral administration of from 10 mg to 2000 mg/day, preferably 10 to 1000 mg/day, more preferably 50 to 600 mg/day, in two to four (preferably two) divided doses, to block tumor growth.

Further, the methods of present invention can be used in conjunction with other chemotherapeutic agents or radiation therapy. The chemotherapeutic agent and/or radiation therapy can be administered according to therapeutic protocols well known in the art. It will be apparent to those skilled in the art that the administration of the chemotherapeutic agent and/or radiation therapy can be varied depending on the disease being treated and the known effects of the chemotherapeutic agent and/or radiation therapy on that disease. Also, in accordance with the knowledge of the skilled clinician, the therapeutic protocols (e.g., dosage amounts and times of administration) can be varied in view of the observed effects of the administered therapeutic agents (i.e., antineoplastic agent or radiation) on the patient, and in view of the observed responses of the disease to the administered therapeutic agents.

In methods of the present invention, a HSP90 inhibitor is administered to cells in conjunction with a cytotoxic agent. Further, when the HSP90 inhibitor is used in conjunction with a microtubule-affecting agent, for treatment of cell proliferative disorders associated with wild-type Rb cells, the microtubule-affecting agent is given first, followed by the HSP90 inhibitor. In cell disorders associated with Rb negative or deficient cells, the administration of the HSP90 inhibitor and cytotoxic agent is schedule independent. Further, if the HSP90 inhibitor is used in conjunction with a topoisomerase II inhibitor, such as doxorubicin in either wild-type Rb cells or Rb negative or deficient cells, the doxorubicin can be given before, or after administration of the HSP90 inhibitor.

The HSP90 inhibitor may be administered orally to generate and maintain good blood levels thereof, while the chemotherapeutic agent may be administered intravenously. The determination of the mode of administration and the advisability of administration, where possible, in the same pharmaceutical composition, is well within the knowledge of the skilled clinician. The initial administration can be made according to established protocols known in the art, and then, based upon the observed effects, the dosage, modes of administration and times of administration can be modified by the skilled clinician.

The particular choice of HSP90 inhibitor, and cytotoxic agent will depend upon the diagnosis of the attending physicians and their judgement of the condition of the patient and the appropriate treatment protocol.

The HSP90 inhibitor, and cytotoxic agent may be administered concurrently (e.g., simultaneously, essentially simultaneously or within the same treatment protocol) or sequentially, depending upon the nature of the proliferative disease, the Rb status of the cells associated with the condition being treated, the condition of the patient, and the actual choice of cytotoxic agent to be administered in conjunction with the HSP90 inhibitor. Thus, the HSP90 inhibitor may be administered first followed by the administration of the cytotoxic agent; or the cytotoxic agent may be administered first followed by the administration of the HSP90 inhibitor. The determination of the order of administration, and the number of repetitions of administration of each therapeutic agent during a treatment protocol, can be determined using the disclosures contained within the present specification and the knowledge of a skilled physician after evaluation of the disease being treated and the condition of the patient.

The attending clinician, in judging whether treatment is effective at the dosage administered, will consider the general well-being of the patient as well as more definite signs such as relief of disease-related symptoms, inhibition of tumor growth, actual shrinkage of the tumor, or inhibition of metastasis. Size of the tumor can be measured by standard methods such as radiological studies, e.g., CAT or MRI scans, and successive measurements can be used to judge whether or not growth of the tumor has been retarded or even reversed. Relief of disease-related symptoms such as pain, and improvement in overall condition can also be used to help judge effectiveness of treatment.

The following examples are not limiting and are merely representative of various aspects and features of the present invention. All references referred to above and below are incorporated herein by reference.

EXAMPLES

Example 1

Growth Inhibition by Combinations of 17-AAG and Cytotoxic Agents

A. General Methods:

Cell Culture:

The human breast cancer cell lines SKBr-3 and BT-549 were obtained from the American Type Culture Collection (Rockville, Md.). Cell lines were maintained in DMEM/F2/1 media supplemented with 10% heat inactivated fetal bovine serum (BRL), 2 mM glutamine and 50 U/ml each of penicillin and streptomycin. All cells were incubated at 37° C. in 5% $CO_2$.

Drug Treatment of Cell Lines:

Cells were plated onto 100 mm tissue culture plates at a density of $2\times10^6$ for 48 h and then treated with CNF-101 (17-AAG), Taxol®, doxorubicin, cisplatin, or combinations of CNF-101 and Taxol®, doxorubicin or cisplatin or equal concentrations of the vehicle (FIGS. 1A–C). For longer drug exposure times, media with drug or vehicle were exchanged every 48 h. Synergistic effects were confirmed by isobologram analysis as developed by Chou and Talalay, and described in Chou T. C., et al., 1994, *J. Natl. Cancer Inst.*, 86: 1517–24.

Antiproliferative Index:

Cells ($2\times10^5$) were plated onto 6-well dishes and treated with the indicated drug(s) or DMSO vehicle for 96 h (FIGS. 1A–C). Drug and media were exchanged every 48 h. After 96 h, media was removed, cells were washed with PBS and harvested. Cells were counted on a Coulter Counter. Dose curves were plotted as a logarithmic function of cell number versus concentrations.

B. Results:

The addition of CNF-101 to cultured breast cancer cells enhanced the growth inhibition caused by several chemotherapeutic agents. These include the DNA intercalating antibiotic doxorubicin, the microtubule-affecting agent paclitaxel and the DNA cross-linking agent cisplatin. These studies were performed at doses that cause minimal growth inhibition of each drug alone in order to demonstrate potential additive or synergistic effects, since higher doses of either drug produced complete growth inhibition induced by CNF-101 or the cytotoxic drug. The addition of 1–10 nM to cisplatin in SKBr-3 breast cancer cells caused growth inhibition that was additive. In contrast, treatment of SKBr-3 breast cancer cells with CNF-101 with Taxol® or doxorubicin caused synergistic growth inhibitory effects (FIGS. 1A–C).

In cells that contain high HER2 these effects are more pronounced. Mathematical analysis by isobologram confirmed synergistic effects.

Example 2

Synergistic Effects of Taxol® and CNF-101 (17-AAG) are Due to Enhanced Induction of Apoptosis A. General Methods:

Apoptotic Scoring:

After treatment with drug, as described herein, apoptosis was scored by the presence of nuclear chromatin condensation and DNA fragmentation and evaluated with fluorescence microscopy. Cells were harvested and fixed in 100% ETOH at −20° C. for 10 min. After washing twice with PBS, nuclei were dual stained with 2 μg/ml of the dye bisbenzimide trihydrochloride (Hoechst #33258) and anti-tubulin antibody (green fluorescence). Anti-tubulin antibody was purchased from Sigma Chemical Co. (St. Louis, Mich.). Two hundred cells were counted for each experiment in five different fields and evaluated for apoptotic score (apoptotic nuclei/all nuclei times 100%) (see, FIGS. 2–4 and FIGS. 6–8). Each experiment was repeated in triplicate.

Schedule Dependence in $Rb^+$ or $Rb^-$ Cells

Breast cancer cells with intact Rb (SKBR-3) or mutated, inactive Rb (BT-549) were treated with vehicle or 10 nM Taxol® for 4 h followed by 50 nM CNF-101 or vehicle for an additional 12–24 h. Alternatively, the order in which the two drugs were given was reversed. Apoptosis was determined as described above and the results are shown in FIGS. 6 and 7.

The schedule dependence of synergy between CNF-101 and the DNA-damaging agent, doxorubicin was also determined (FIG. 8). SKBR-3 cells were treated with vehicle, 100 nM or 200 nM doxorubicin followed by 50 nM CNF-101 or vehicle for an additional 12 h. Alternatively, the order in which the two drugs were given was reversed.

Figure 2:
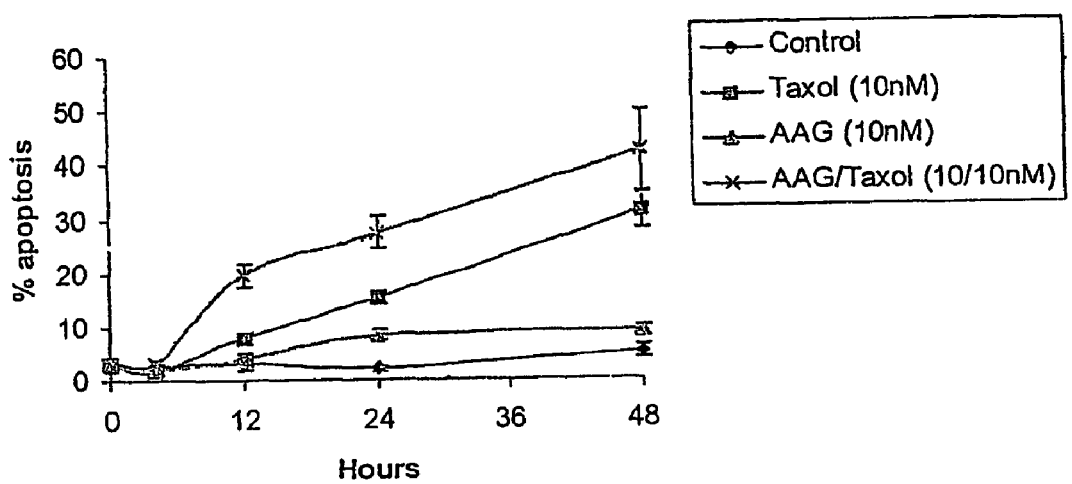
FIG. 2 shows a time course of apoptosis induced by low concentrations of CNF-101 (17-AAG), Taxol®, or a combination of both in SKBR-3 breast cancer cells.
Figure 3A:
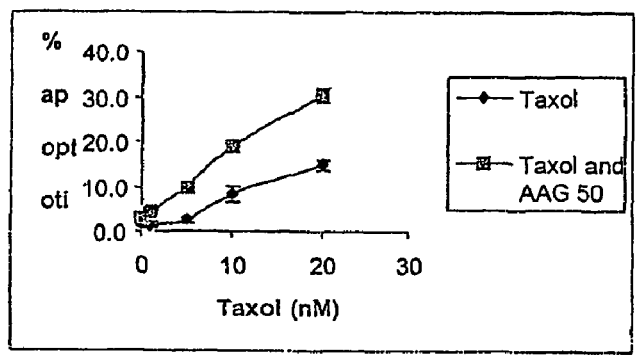
FIGS. 3A and B shows dose-dependence of apoptosis induced by low concentrations of CNF-101 (17-AAG), Taxol® or a combination of both in SKBR-3 breast cancer cells.
Figure 3B:
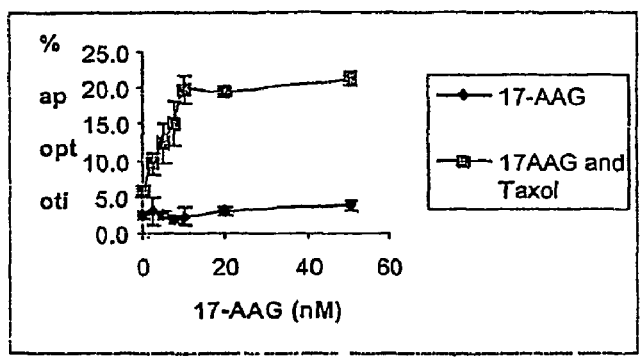
FIG. 3B shows increasing concentrations of CNF-101 (17-AAG) with or without 10 nM of Taxol®.

B. Results:

In order to determine whether the enhanced growth inhibitory effects were due to increased apoptosis, the degree of apoptosis induced by either CNF-101 or paclitaxel or the combination of both agents was measured over time. Continuous exposure to CNF-101 alone showed a relatively small increase in number of apoptotic nuclei (2.75% to 9% compared to untreated cells 2% to 5.1%), but a drastic increase in apoptosis by paclitaxel ($IC_{50}$) alone 2% to 27.5%. The combination of both agents further increased this degree of apoptosis 3% to 42.5%. The effects of the combination compared with either agent alone were most pronounced at 12 h and 24 h. Evaluation of apoptosis at 4 h showed minimal effects on apoptosis (FIG. 2). The percent of apoptosis was also determined for increasing concentrations of Taxol® with or without 50 nM of CNF-101 or with increasing concentrations of CNF-101 with or without 10 nM of Taxol® (FIG. 3).

Example 3

Differential Effects of Taxol®, CNF-101 (17-AAG) and the Combination of Both Agents On Spindle Formation and Apoptosis in SKBR-3 Cells The effects of Taxol®, CNF-101 and a combination of the two agents on nuclear fragmentation (a marker of apoptosis) and mitotic spindle formation in SKBR-3 cells were assessed. The results are shown in FIG. 4.

Analysis by confocal microscopy of SKBr-3 cells treated with 10 nM Taxol® for 4 h followed by 50 nM CNF-101 or vehicle and dual-stained of with Hoechst DAPI, blue stain) and anti-tubulin antibody (green fluorescence) showed that cells treated with neither drug or with CNF-101 alone displayed no significant apoptosis at 12 h (FIG. 4). In these sections, 4% of cells were undergoing mitosis and the mitotic cells appeared normal. In contrast, treatment with Taxol® alone caused an increase in the mitotic index with all the mitotic cells appearing to have damaged spindles, but little evidence of apoptotic nuclear fragmentation was seen. In cells treated with both agents, mitosis was compromised to a similar degree as with Taxol® alone but in addition a significant level of nuclear breakdown was observed, as indicated by the blue stained fragments in the lower right panel. Therefore, these results indicate that Taxol® acts by disrupting mitotic spindle formation. Further, CNF-101 has no effect on the spindle but instead enhances the cellular apoptotic response to spindle disruption.

Example 4

Comparison of the Effects of CNF-101 (17-AAG), Taxol® and a Combination of Both Agents On Progression through the Cell Cycle in SKBR-3 Breast Cancer Cells. Effect of Order of Administration of CNF-101 and Taxol®

A. General Methods:

SKBR-3 cells were treated with vehicle or 10 nM Taxol® for 4 h followed by 50 nM CNF-101 for an additional 12–24 h. To measure the effect of scheduling, the order in which the two drugs were given was reversed. Cells were trypsinized and analyzed by DNA content (an indication of cell cycle status) by fluorescent staining and FACS analysis. Cell cycle distribution was assayed according to Nusse et al., 1990, *Cytometry*, 11: 813, with a Becton Dickinson fluorescence-activated cell sorter and analyzed by Cell Cycle Multi-cycle system (Phoenix Flow System, San Diego, Calif.).

Figure 5:
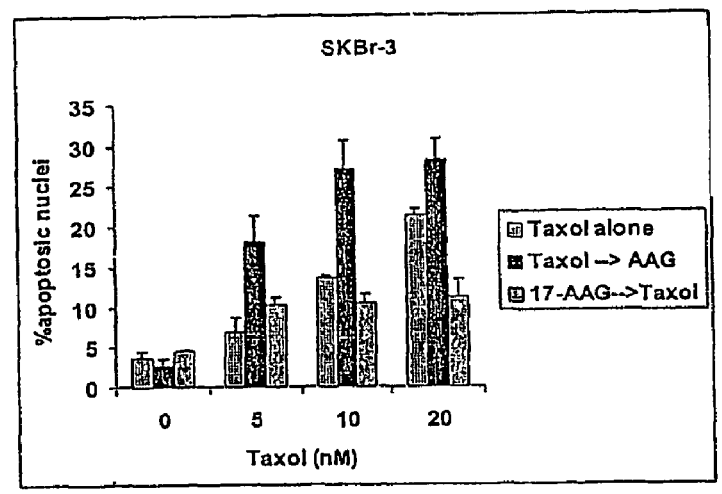
FIG. 5 shows cell cycle analysis of cells treated with Taxol® followed by CNF-101 (17-AAG), or CNF-101 (17-AAG) followed by Taxol®.

B. Results:

Vehicle-only treated cells (FIG. 5—upper left panel) were primarily in the $G_1$ phase of the cell cycle. Treatment with CNF-101 alone slightly enhanced the $G_1$ fraction (FIG. 5—upper right panel). By contrast, Taxol® treatment caused a massive $G_2$-M arrest characteristic of a mitotic block induced by spindle damage, as expected for this agent (FIG. 5—lower left). When CNF-101 was given after Taxol®, cells were blocked in G2-M. However, when CNF-101 was given first, the Taxol® G2-M block was superceded by a CNF-101-induced G1 block (FIG. 5—lower right panel).

Example 5

Schedule Dependence of Apoptosis Induced by Cytotoxic Agents $Rb^+$ and Rb Cells A. General Methods:

Breast cancer cells with intact Rb (SKBR-3) or mutated, inactive Rb (BT-549) were treated with vehicle or 10 nM Taxol® for 4 h followed by 50 nM CNF-101 or vehicle for a further 12–24 hrs (Taxol®→CNF-101). Alternatively, the order in which the two drugs were given was reversed. (CNF-101→Taxol®).

B. Results:

Using the $Rb^+$ line SKBR-3, when Taxol® was followed by CNF-101, significant enhancement of apoptosis was seen. By contrast, reversal of the order of drug administration resulted in no augmentation of Taxol® activity at low Taxol® concentrations and actually caused loss of Taxol® killing at 20 nM Taxol®.

Figure 6:
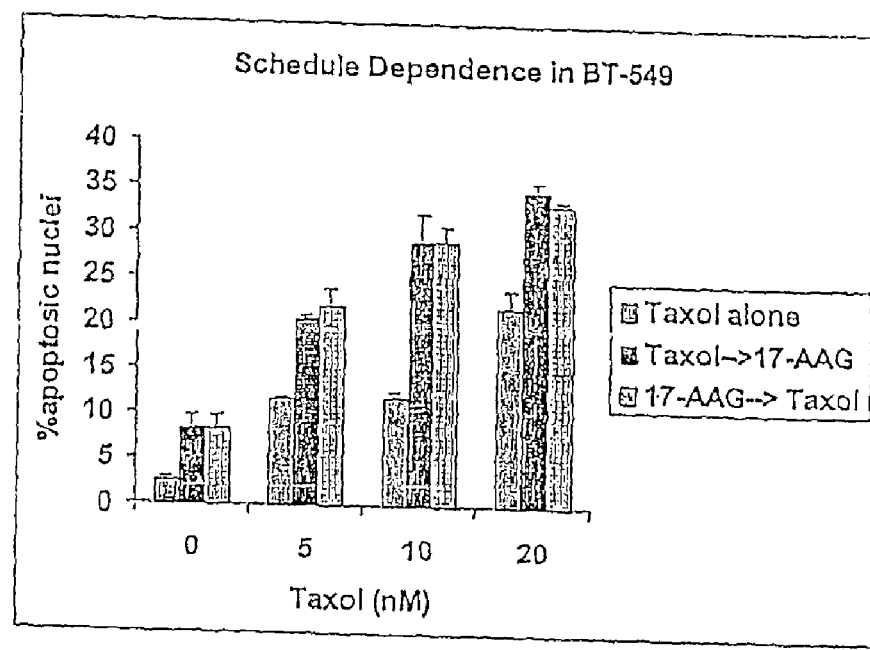
FIG. 6 shows administration of CNF-101 (17-AAG) and Taxol® is not schedule dependent in RB negative cells.

Quite different outcomes were seen when the Rb-negative BT-49 cell line was tested. In this case, CNF-101 significantly enhanced Taxol® activity whether it was given before or after the Taxol®. The data from these experiments are shown in FIG. 6.

Figure 7:
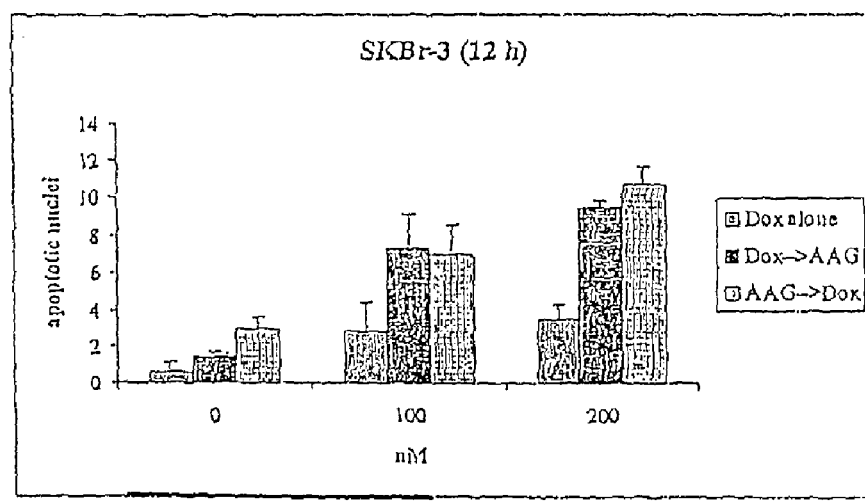
FIG. 7 shows administration of CNF-101 (17-AAG) and doxorubicin is not schedule or RB dependent.

The schedule-dependence of synergy between CNF-101 and cytotoxic agents only applied to G2-M-acting drugs, such as Taxol®. When CNF-101 was combined with a DNA damaging agent, doxorubicin, no effect or the order of drug administration was seen, even in $Rb^+$ cells. These data are shown in FIG. 7.

All patents and publications mentioned in the specification are indicative of the levels of skill of those skilled in the art to which the invention pertains. All references cited in this disclosure are incorporated by reference to the same extent as if each reference had been incorporated by reference in its entirety individually. None of the references are admitted to be prior art.

One skilled in the art would readily appreciate that the present invention is well adapted to carry out the objects and obtain the ends and advantages mentioned, as well as those inherent therein. The methods and compositions described herein as presently representative of preferred embodiments are exemplary and are not intended as limitations on the scope of the invention. Changes therein and other uses will occur to those skilled in the art, which are encompassed within the spirit of the invention, are defined by the scope of the claims.

It will be readily apparent to one skilled in the art that varying substitutions and modifications may be made to the invention disclosed herein without departing from the scope and spirit of the invention. Thus, such additional embodiments are within the scope of the present invention and the following claims.

The invention illustratively described herein suitably may be practiced in the absence of any element or elements, limitation or limitations which is not specifically disclosed herein. Thus, for example, in each instance herein any of the terms "comprising", "consisting essentially of" and "consisting of" may be replaced with either of the other two terms. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments, optional features, modification and variation of the concepts herein disclosed may be resorted to by those skilled in the art, and that such modifications and variations are considered to be within the scope of this invention as defined by the description and the appended claims.

In addition, where features or aspects of the invention are described in terms of Markush groups or other grouping of alternatives, those skilled in the art will recognize that the invention is also thereby described in terms of any individual member or subgroup of members of the Markush group or other group.

Other embodiments are within the following claims.

The invention claimed is:

1. A method for destroying cells having a cell proliferative disorder with wild-type retinoblastoma gene (Rb), comprising the steps of
    (a) administering to said cells a G2/M-acting cytotoxic agent; and
    (b) administering a compound capable of inhibiting eukaryotic heat shock protein 90 (HSP90) function;
    wherein said GM- acting agent is administered before the HSP90 inhibitor such that the cytotoxicity is enhanced compared to cytotoxicity of the cytotoxic agent and the compound capable of inhibiting HSP90 function administered at the same time.

2. The method of claim 1, wherein said cytotoxic agent is selected from the group consisting of a microtubule-affecting agent, a DNA cross-linking agent and a topoisomerase II inhibitor.

3. The method of claim 2, wherein said cytotoxic agent is a microtubule-affecting agent selected from the group consisting of a vinca alkaloid and a taxane.

4. The method of claim 3, wherein said cytotoxic agent is paclitaxel or a derivative thereof.

5. The method of claim 1, wherein said HSP90 inhibitor is selected from the group consisting of an ansamycin, radicicol, and a synthetic compound which binds to the ATP-binding site of HSP90.

6. The method of claim 5, wherein the HSP90 inhibitor is 17-allyl-amino 17-demethoxy geldanamycin or a derivative thereof.

7. A method for the treatment of cell proliferative disorders associated with wild-type retinoblastoma gene (Rb) cells, in an animal in need of such treatment, comprising the following steps:
    (a) administering to said cells a G2/M-acting cytotoxic agent effective for treating the cell proliferative disorder; and
    (b) administering a compound capable of inhibiting eukaryotic heat shock protein 90 (HSP90 ) function;
    wherein said $G_2$/M-acting agent is administered before the HSP90 inhibitor such that the cytotoxicity is enhanced compared to cytotoxicity of the cytototoxic agent and the compound capable of inhibiting HSP90 function administered at the same time.

8. The method of claim 7, wherein said cytotoxic agent is selected from the group consisting of a microtubule-affecting agent, a DNA cross-linking agent and a topoisomerase II inhibitor.

9. The method of claim 8, wherein said cytotoxic agent is selected from the group consisting of a vinca alkaloid and a taxane.

10. The method of claim 9, wherein said cytotoxic agent is paclitaxel of a derivative thereof.

11. The method claim 7, wherein said HSP90 inhibitor is selected from the group consisting of an ansamycin, radicicol, and a synthetic compound which binds to the ATP-binding site of HSP90.

12. The method of claim 11, wherein said HSP90 inhibitor is 17-allyl-amino 17-demethoxy geldanamycin or a derivative thereof.

13. The method of claim 7, wherein said animal is a mammal.

14. The method of claim 13, wherein said mammal is a human.

15. The method of claim 7, wherein said cell proliferative disorder is breast cancer.

UNITED STATES PATENT AND TRADEMARK OFFICE
CERTIFICATE OF CORRECTION

PATENT NO. : 7,211,562 B2  Page 1 of 1
APPLICATION NO. : 10/415878
DATED : May 1, 2007
INVENTOR(S) : Rosen et al.

It is certified that error appears in the above-identified patent and that said Letters Patent is hereby corrected as shown below:

Column 20:
Claim 7, Line 16 should read: --compared to cytotoxicity of the cytotoxic agent and the--

Signed and Sealed this

Twelfth Day of June, 2007

JON W. DUDAS
*Director of the United States Patent and Trademark Office*